United States Patent [19]

Cole

[11] Patent Number: 5,900,420
[45] Date of Patent: May 4, 1999

[54] METHOD FOR TREATING CHRONIC FATIGUE SYNDROME AND FIBROMYALGIA WITH BUPRENORPHINE

[76] Inventor: William L. Cole, 1015 Canter Rd., Atlanta, Ga. 30324

[21] Appl. No.: 09/099,900

[22] Filed: Jun. 18, 1998

Related U.S. Application Data

[60] Provisional application No. 60/050,157, Jun. 19, 1997, and provisional application No. 60/056,571, Aug. 21, 1997.

[51] Int. Cl.$^6$ .................................................. A61K 31/44
[52] U.S. Cl. ............................................................ 514/289
[58] Field of Search ............................................ 514/289

[56] References Cited

U.S. PATENT DOCUMENTS

| | | | |
|---|---|---|---|
| 5,013,739 | 5/1991 | Bihari et al. ............................ | 514/282 |
| 5,545,670 | 8/1996 | Bissbort et al. ........................ | 514/562 |

OTHER PUBLICATIONS

Borenstein, D., Prevalence and Treatment Outcome of Primary and Secondary Fibromyalgia In Patients With Spinal Pain, *Spine*, vol. 2, No. 7, pp. 796–800, Apr. 1, 1995 (Abstract Only).
Budavari, S. et al., *The Merck Index—An Encyclopedia of Chemicals, Drugs and Biologicals*—1487—Eleventh Edition, 1989 p. 228.
Fukada, et al. The Chronic Fatigue Syndrome: A Comprehensive Approach to Its Definition and Study. *Annals of Internal Medicine*. vol. 121(12), Dec. 15, 1994. pp. 953–959.
Goodman & Gilman's *The Pharmacological Basis of Therapeutics*. 1996, pp. 618–622.
Gylys. Pharmacology. *The Journal of Cardiovascular Nursing*. vol. 12(3), Apr. 1998. pp. 52–56.
Holmes, et al. Chronic Fatigue Syndrome: A Working Case Definition. *Annals of Internal Medicine*. vol. 108. 1988, pp. 387–389.
Calabrese, et al. "Chronic Fatigue Syndrome", American Family Physician, vol. 45, No. 3, pp. 1205–1213 (1992).
Oliveto, et al. "Buprenorphine", The new pharmacotherapies, pp. 255–265 (1992).
Cox, et al. "Red blood cell magnesium and chronic fatigue syndrome" The Lancet, vol. 337, pp. 757–760 (1991).
CDC CFS Research Group, Center Disease Control, Atlanta, GA, "Chronic Fatigue Syndrome Research at the CDC", the CFIDS Chronicle Physician's Forum, pp. 50–77 (1992).
Collinge, William "Recovering from Chronic Fatigue Syndrome: A guide to self–empowerment" pp. 40–41 (1993).
Cheney, et al., "The diagnosis of chronic fatigue syndrome: an assertive approach", the CFIDS Chronicle Physician's Forum, pp. 13–19 (1992).
Vanderzalm, Lynn, "Riding the emotional roller–coaster of CFIDS", The CFIDS Chronicle, pp. 19–21 (1997).
Peterson et al., "Effects of mild exercise on cytokines and cerebral blood flow in chronic fatigue syndrome patients" Clin. Diagn. Lab. Immunol. vol. 1, No. 2 pp. 222–226 (1994).

Mawle, A.C., "Chronic fatigue syndrome", Immunological investigations, 26(1 and 2) pp. 269–273 (1997).
DiPino, et al., "Neurocognitive functioning in chronic fatigue syndrome", neuropsychology review, vol. 6, No. 1, pp. 47–60 (1996).
Cleare, et al. "Contrasting neuroendocrine responses in depression and chronic fatigue syndrome", Jour. Affective Disorders 35, pp. 283–289 (1995).
"Chronic Fatigue Syndrome", National Institute of Allergy and Infectious Diseases, Spring 1994.
Kantrowitz, et al. "Chronic fatigue syndrome 2: treatment and future research", Behav. Med., vol. 21, pp. 17–23 (1995).
Suhadolnik, et al. "Biochemical evidence for a novel low molecular weight 2–5A–Dependent RNase L in Chronic Fatigue Syndrome", Jour. of Interferon and Cytkine Research vol. 17, pp. 377–385 (1997).
Bearn, et al. "Neurobiological aspects of the chronic fatigue syndrome", Eur. Jour. of Clin. Investigation, vol. 24, pp. 79–90 (1994).
Dinan, et al. "Blunted serotonin–mediated activation of the hypothalmic–pituitary–adrenal axis in chronic fatigue syndrome", Psychoneuroendocrinology, vol. 22, No. 4, pp. 261–267 (1997).
McBride, et al., "Treatment of chronic fatigue syndrome", Brit. Med. Bulletin, vol. 47, No. 4, pp. 895–907 (1991).
Koopman, "Cytokines and their receptors in arthritis and allied conditions" (1997).
Goldstein, Jay A., "The diagnosis of chronic fatigue syndrome as a limbic encephalopathy", The CFIDS Chronicle Physicians Forum, pp. 20–31 (1992).
Hendrick, Bill, "The enemy within", The Atlanta Jour. and Constitution, Section E, Jun. 17, 1995.
Cleare, Anthony J., "Letters to the Editor", Can. Jour. of Psychiatry, vol. 41, No. 2 (1996).
Mello, Nancy K. "Comparison of Buprenorphine and Methadone Effects on Opiate Self–Administration in Primates", Jour. of Pharmacology and Experimental Therapeutics, vol. 225, No. 2 (1983).
English, Thomas L. "Skeptical of Skeptics", J.A.M.A. ed. 27, vol. 265, No. 8, p. 964 (1991).
Komaroff, et al. "An Examination of the Working Case Definition of Chronic Fatigue Syndrome", Am J. Med., vol. 100, pp. 56–64 (1996) (Abstract only).
Farmer, et al. "Screening for Psychiatric Morbidity in Subjects Presenting with Chronic Fatigue Syndrome", Br. J. Psychiatry, vol. 168, pp. 354–358 (1996) (Abstract only).
Cannon, et al. "Interleukin–1 beta, interleukin–1 receptor antagonist, and soluble interleukin–1 receptor type secretion in chronic fatigue syndrome", J. Clin. Immunol., vol. 17, pp. 253–261 (1997) (Abstract only).

(List continued on next page.)

*Primary Examiner*—Raymond Henley, III
*Attorney, Agent, or Firm*—Jones & Askew, LLP

[57] ABSTRACT

The present invention encompasses methods for treating chronic fatigue syndrome and fibromyalgia by administering buprenorphine or a salt thereof. The compound may optionally be administered in a pharmaceutical composition. Preferred compositions for delivery of the buprenoiphine are sublingual lozenges and transdermal gel.

14 Claims, No Drawings

OTHER PUBLICATIONS

Bodkin, et al. "Buprenorphine Treatment of Refractory Depression", J. Clin. Psychopharmacol., vol. 15/No. 1, pp. 49–57 (1995).

Mawle et al. "Immune Reponses Associated with Chronic Fatigue Syndrome: A case–control study" J. Infect. Dis., vol. 175, pp/ 136–141 (1997) (Abstract only).

Marcel, et al. "Cognitive Deficits in Patients with Chronic Fatigue Syndrome" Bio. Psychiatry, vol. 40, pp. 535–541 (1996) (Abstract only).

Cheng, et al. "N–cubylmethyl Substituted Morphinoids as Novel Narcotic Antagonists" Bioorg. Med. Chem., vol. 4, pp. 73–80 (1996) (Abstract only).

"Chronic Fatigue Syndrome Information for Physicians", NIH Publication No. 96–484, Sep. 1996.

Lewis, et al., "Buprenorphine: Background to its development as a treatment for opiate dependence", J.D. Blaine, Ed., Buprenorphine: Alternative treatment for opioid dependence. NIDA Monograph No. 121, pp. 5–11 (1992) (Abstract only).

Banys, et al., "An open trial of low dose buprenorphine in treating methadone withdrawl", Journal of Substance abuse Treatment pp. 9–15 (1994) (Abstract only).

Bevan, et al. "Sublingual bioavailability of buprenorphine at analgesic doses", L.S. Harris, ed., Problems of drug dependence, 1995: Proceedings of the 57th annual scientific meeting, college on problems of drug dependence. NIDA research monograph 162 (1995) (Abstract only).

Wallenstein, et al. "Clinical analgesic assay of sublingual buprenorphine and intramuscular morphine", Problems of drug dependence, 1981: Proceedings of the 43rd annual scientific meeting, committee on problems of drug dependence. NIDA research monograph 41 (1981) (Abstract only).

Jeffcoat, et al. "Human disposition of intravenous, oral and sublingual [3H] buprenorphine", L. Harris, ed. Problems of drug dependence, 1992: Proceedings of the 54th annual scientific meeting, college on problems of the drug dependence. NIDA research monograph 132 (1993) (Abstract only).

Banys, et al. "Pilot study with low–dose buprenorphine", L. Harris, ed. Problems of drug dependence, 1991: Proceedings of the 53rd annual scientific meeting, committee on problems of drug dependence. NIDA research monograph 119, p. 360 (1995) (Abstract only).

Mendelson, et al. "Buprenorphine pharmacokinetics: Bioavailability of an 8mg sublingual tablet formulation", L.S. Harris, ed. Problems of drug dependence, 1995: Proceedings of the 57th annual scientific meeting, college on problems of drug dependence. NIDA research monograph 162, p. 112 (1995) (Abstract only).

Cone, et al. "Elevated drug saliva levels suggest a 'sepot–like' effect in subjects treated with sublingual buprenorphine", L. Harris, ed. Problems of drug dependence, 1990: Proceedings of the 52nd annual scientific meeting, college on problems of drug dependence. NIDA research monograph 105, p. 569 (1995) (Abstract only).

"Prefin* brand of Buprenorphine Hydrochloride", *RxMed*, pp. 1–6, Website: http://www.rxmed.com/monographs2/preferin.html (1997).

"What Is CFIDS.M.E.?", WECAN, Inc., pp. 1–3 (1997) Website: http://www.community–care.org.UK/wecan/handout.html.

"The Facts About Chronic Fatigue Syndrome", *Centers for Disease Control and Prevention—National Center For Infectious Diseases—Atlanta, Georgia* (Mar. 1995) pp. 1–13 Website:http://www.dds.nl/~me–net/meweb/cdcfacts.txt.

"The Quality Of Mercy", *U.S. News On Line*, pp. 1–8 (1997) Website:http://www.usnews.com/usnews/issue/970317/17pain.htm.

"Table 5. Dosing for Opioid Analgesics", pp. 1–3 (1997) Website: http://www.roxane.com/Roxane/RPI/Healthcare-ProfessionalLibrary/AHCPR.apmpqt5.html.

"Narcotics and Other Analgesic Drugs", pp. 1–2 (1998) Website: http://eja.anes.hscsyr.edu/vat/narcotics.html.

"Buprenorphine May Soon Be Herion Treatment Option", John A. Bowersox, NIDA Notes Contributing Writer, pp. 1–3, Website: http://www.nida.hid.gov.NIDA_Notes/NNVol1N1.Bupren.html (1998).

The CFIDS Chronicle, vol. 10 No. 3, Summer 1997—pp. 1–65.

The CFIDS Chronicle, vol. 11 No. 1 –Jan./Feb. 1998—pp. 1–49.

METHOD FOR TREATING CHRONIC FATIGUE SYNDROME AND FIBROMYALGIA WITH BUPRENORPHINE

This application claims priority under 35 U.S.C. 119(e) for Provisional Applications 60/050,157 filed Jun. 19, 1997 and 60/056,571 filed Aug. 21, 1997.

FIELD OF THE INVENTION

The present invention relates to the use of buprenorphine for the treatment of chronic fatigue syndrome, also referred to as chronic fatigue immune deficiency syndrome, and fibromyalgia. In addition, the present invention relates to two preferred delivery systems for the treatment of chronic fatigue syndrome with buprenorphine. More specifically, the first system of delivery of buprenorphine is via a sublingual lozenge. The second system involves a transdermal gel system, whereby a specific quantity of a gel containing the buprenorphine is applied to any vascular area of the body.

BACKGROUND OF THE INVENTION

Chronic fatigue syndrome (CFS) is a clinically defined condition characterized by severe disabling flu-like fatigue and a combination of symptoms that include impairment in concentration and short-term memory, sleep disturbances, and musculoskeletal pain. No specific test exists to diagnose chronic fatigue syndrome. Therefore, the presence of chronic fatigue requires a clinical evaluation to identify underlying conditions that may require treatment. A patient should be evaluated for depression and other psychiatric disorders; alcohol or other substance abuse; and current use of prescription and over-the-counter medications and food supplements. In addition, a complete laboratory work-up should be performed to rule out the possibility of any existing medical problems. The central issue is whether chronic fatigue syndrome or any subset of the syndrome is a pathologically discrete entity or a debilitating but nonspecific condition shared by many different illnesses.

The study of chronic fatigue syndrome is problematic because, to date, no tests have consistently proven or demonstrated this illness. Tests should be directed toward confirming or excluding other etiologic possibilities. Clarification of the relation between chronic fatigue syndrome and neuropsychiatric syndromes are particularly important. These latter disorders are the source of confusion in studies of chronic fatigue syndrome as these disorders are diagnosed more frequently in populations affected by chronic fatigue than in the general population. The extent to which the features of chronic fatigue syndrome are generic features of chronic fatigue and deconditioning due to physical inactivity common to a diverse group of illnesses must be established.

Fibromyalgia (FMS) is a chronic rheumatic condition characterized by systemic body pain and uncontrollable fatigue. Many other symptoms are associated with fibromyalgia, such as irritable bowel, headaches, sleep disorders, and poor circulation.

Chronic fatigue syndrome and fibromyalgia remain serious problems for the general population which are not only difficult to diagnose and have no known effective treatment. Although many medications are commonly used to treat these conditions, there are no known medications which permanently resolve the symptoms of either chronic fatigue syndrome or fibromyalgia. In addition, many of the currently used medications produce side effects ranging from mild side effects, e.g., drowsiness, dizziness, and nausea to serious side effects, e.g., addiction and liver damage.

Some of the more common medications currently employed to treat chronic fatigue syndrome and/or fibromyalgia include, but are not limited to, analgesics, hypnotics, immune suppressants, various other prescribed medications, and an array of non-prescription medications.

Analgesics include nonsteroidal anti-inflammatory drugs which can relieve pain. Some preparations of analgesics are available as over-the-counter medications and have been prescribed for CFS and fibromyalgia patients for symptomatic relief. An analgesic that is sometimes prescribed for CFS and FMS patients is cyclobenzaprine. It is generally prescribed for the relief of skeletal muscle spasm and its associated signs and symptoms.

Benzodiazepines are one commonly used type of hypnotics. This group of drugs is sometimes prescribed to treat seizures, but it is prescribed for CFS patients as a treatment for various sleep disorders. Examples of benzodiazapines used in the treatment of chronic fatigue syndrome and fibromyalgia are Klonopin™, Valium™, Zanax™, Ativan™, and Dalmane™. A non-benzodiazepine hypnotic drug that has sometimes been prescribed to relieve sleep problems for CFS patients is Zolpidem.™

Azathioprine is an immune suppressant that has been prescribed to CFS and FMS patients. Presumably, these drugs have been employed based on the unsubstantiated theory that CFS is characterized by some underlying immune dysfunction. Such a use is purely experimental and, in view of the degree of toxicity associated with these agents, is inappropriate for the treatment of CFS and FMS.

Some of the various other prescription drugs given to treat CFS and FMS patients include Naltrexone™, an opioid antagonist, sodium retention agents/beta blockers, calcium channel blockers/histamine blockers, anti-depressants, allergy medications, and acute anxiety medications. Most of these drugs are either inappropriate for the treatment of CFS and FMS either because they are not effective or because of the significant side effects associated with their use.

Some of the non-prescription medications given to patients with CFS and FMS include herbal preparations, and vitamin and mineral supplements. Although the potential medicinal value of various herbs is promising, it is difficult, if not impossible, to assess the validity of scientific claims regarding these substances. In addition, vitamin/mineral supplements may demonstrate some positive results but none have any scientifically demonstrated clinical value. In addition, these supplements may be toxic if taken in high doses.

Thus, it is clear that chronic fatigue syndrome and fibromyalgia are debilitating diseases for which no known effective treatment exist. What is needed, therefore, is a composition that is effective in treating chronic fatigue syndrome and fibromyalgia. Also needed are methods for delivery which would allow for easy and regimented application.

SUMMARY OF THE INVENTION

In accordance with the present invention, compositions and methods are provided that are effective for controlling the symptoms of chronic fatigue syndrome and fibromyalgia. The present invention includes the use of buprenorphine for the alleviation of the major debilitating symptoms of both chronic fatigue syndrome and fibromyalgia.

Buprenorphine, 17-(cyclopropylmethyl)-α-(1,1-dimethylethyl)-4,5-epoxy- 18,19-dihydro-3-hydroxy-6-methoxy-α-methyl-6,14-ethenomorphinan-7-methanol, is a derivative of the narcotic thebaine and is currently classified as a Level V narcotic under the Controlled Substance Act. It is an opioid agonist/antagonist useful as an analgesic and respiratory stimulant. According to the present invention, buprenorphine may be administered orally, sublingually, parenterally, intramuscularly, intravenously, interperitoneally, topically, transdermally, and the like.

The present invention also encompasses two preferred delivery methods, including a sublingual lozenge system and a transdermal gel system. The sublingual lozenge system provides the delivery of buprenorphine via a sublingual lozenge. The dosage ranges from 0.125 mg to 0.5 mg per lozenge, for administration of between approximately two to three lozenges per day. The transdermal gel system provides delivery via a gel system. This application involves applying a standard quantity of a gel containing the buprenorphine to the surface of the body. In one embodiment, the gel is dispensed with a two-sided scoop. One side of the scoop holds 0.5 grams of the gel, while the other side holds 1.0 gram of gel. The buprenorphine is compounded into the gel by methods known to those of skill in the art. (See, for example, Remington's Pharmaceutical Sciences, latest edition, by E. W. Martin, Merck Publ. Co., Easton, Pa.) The dose of buprenorphine ranges from 0.125 mg to 0.50 mg of buprenorphine per gram of gel. The gel is applied to any vascular area of the body. Because of a lower absorption rate, the use of the transdermal gel system will require higher dosing by increasing the number of applications of gel each day. In general, two to six applications will provide an effective dose of buprenorphine.

Other modes of application of buprenorphine include subcutaneous administration as well as intramuscular or intravenous injection. Effective daily doses of buprenorphine for the treatment of chronic fatigue syndrome and fibromyalgia are from about 0.125 mg/day to about 3.0 mg/day. Such dosages are provided throughout the day by administration of buprenorphine or a salt thereof from two to six times during the day. For example, pharmacological effects occur as soon as 15 minutes after intramuscular injection and persist for 6 hours or longer with peak pharmacological effects usually observed at 1 hour.

Accordingly, it is an object of the present invention to provide a method and composition for treating the major symptoms of chronic fatigue syndrome.

It is another object of the present invention to provide a method and composition for treating the major symptoms of fibromyalgia.

It is yet another object of the present invention to provide a method of application of buprenorphine through a sublingual lozenge system.

It is a further object of the present invention to provide a method of application of buprenorphine through a transdermal gel system.

Still another object of this invention is to provide a mode of application which differs from the current available method of application. The injection mode of application differs from either the sublingual lozenge or transdermal gel in both the application and the effect.

DETAILED DESCRIPTION

Chronic fatigue syndrome is a clinically defined condition characterized by severe disabling flu-like fatigue and a combination of symptoms that include impairment in concentration and short-term memory and sleep disturbances. Similarly, fibromyalgia is a clinically defined condition characterized by widespread body pain and uncontrollable fatigue. Certain individuals who had been labeled in the past with diagnoses such as the vapors, neurasthenia, effort syndrome, hyperventilation syndrome, chronic brucellosis, epidemic neuromyasthenia, myalgic encephalomyelitis, hypoglycemia, multiple chemical sensitivity syndrome, chronic candidiasis, chronic mononucleosis, chronic Epstein-Barr virus infection, and postviral fatigue syndrome probably had what we are now calling chronic fatigue syndrome, and the invention contemplates that the present methods can be used to treat these conditions. Chronic fatigue syndrome also produces a wide variety of flu-like symptoms, e.g., low grade fever and musculoskeletal pain. The Centers for Disease Control recently revised the definition of CFS to be more functional wherein the symptom of fatigue refers to severe mental and physical exhaustion, which differs from somnolence or lack of motivation and which is not attributable to exertion or diagnosable disease. In addition the requirement of 6 months duration of fatigue was retained.

There has been no known treatment for either CFS or FMS which has shown effectiveness, although many medications have been utilized in the attempt to end or mitigate symptoms. None of these medications has demonstrated efficacy and often have been associated with serious side effects. Therefore a new treatment for CFS and/or FMS is needed.

The present invention includes composition and methods for effectively alleviating the debilitating symptoms of chronic fatigue syndrome and fibromyalgia. The present invention also encompasses two desired delivery systems for the use of buprenorphine.

More particularly, the present invention includes methods of treating chronic fatigue syndrome and fibromyalgia with buprenorphine. The chemical name for buprenorphine is 17-(cyclopropylmethyl)-alpha-(1,1-dimethylethyl)-4,5-epoxy-18,19-dihydro-3-hydroxy-6-methoxy-alpha-methyl-6,14-ethenomorphinan-7-methanol, (Saipha, 7alpha(S)). It has the following chemical formula:

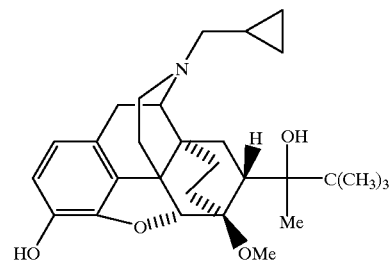

The invention also includes the use of salts of buprenorphine. Buprenorphine hydrochloride is the preferred salt, but other salts of buprenorphine can also be used. Buprenorphine hydrochloride is a white powder, weakly acidic, and with limited solubility in water. As an injectable solution, buprenorphine hydrochloride is a clear, sterile solution having agonist/antagonist analgesic activity. The solution is preferably injected intravenously or intramuscularly.

In one embodiment, the invention comprises administering to a human or animal having chronic fatigue syndrome or fibromyalgia an injectable solution of buprenorphine hydrochloride. Each ml of the solution contains 0.324 mg buprenorphine hydrochloride (equivalent to 0.3 mg buprenorphine), 50 mg anhydrous dextrose, water for injection, and HCl to adjust the pH.

In another embodiment, the invention comprises administering to a human or animal having chronic fatigue syndrome or fibromyalgia a sublingual lozenge containing buprenorphine hydrochloride. Each lozenge contains from about 0.125 mg to 0.5 mg buprenorphine hydrochloride. The lozenges provide an effective dose of buprenorphine for about four to six hours. Thus, the invention contemplates administration of about two to three lozenges per day.

In a third embodiment, the present invention comprises administering to a human or animal having chronic fatigue syndrome or fibromyalgia a transdermal gel containing buprenorphine hydrochloride. The gel contains about 0.125 mg to 0.5 mg of buprenorphine per gram of gel. The gel may be administered in any manner; however, the preferred method of administration is performed using a two-sided scoop. One side of the scoop holds 0.5 grams of the transdermal gel, while the other side holds 1.0 gram of the gel. The transdermal gel is preferably applied to a vascular area of the skin—most preferably to the area near the carotid artery. Due to lower absorption rates via transdermal delivery, higher doses are required as compared to administration sublingually or by injection. Generally, two to six administrations of the gel are sufficient to provide an effective dose of buprenorphine.

The dosage of the compound administered will depend on the condition being treated, the particular compound administered, and other clinical factors, such as the weight and condition of the human or animal to be treated and the route of administration of the compound. It is to be understood that the present invention has application for both human and veterinary use. For other routes of administration, the buprenorphine concentration in the delivery vehicle is adjusted to result in blood levels of the buprenorphine that are roughly equivalent to the blood level resulting from the intravenous administration.

The formulations of present include those suitable for oral, rectal, ophthalmic, (including intravitreal or intracameral) nasal, topical (including buccal and sublingual), vaginal and parenteral (including subcutaneous, intramuscular, intravenous, intradermal, intratracheal, and epidural) administration of buprenorphine. The formulations may conveniently be presented in unit dosage form and may be prepared by conventional pharmaceutical techniques. (See, for example, Pharmaceutical Dosage Forms and Drug Delivery Systems, 6th Edition, Ansel, H. C. et al., Ed, Williams & Wilkens, 1995, which is incorporated herein by reference.) Such techniques include the step of bringing into association the active ingredient (i.e., the buprenorphine compound) and pharmaceutical carriers or excipients. In general, the formulations are prepared by uniformly and intimately bringing into association the active ingredient with liquid carriers or finely divided solid carriers or both, and then, if necessary, shaping the product.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the active ingredient to be administered in a pharmaceutical acceptable carrier. Topical delivery systems include a transdermal patch and a transdermal gel containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns, which is administered in the manner in which snuff is administered, i.e., by rapid inhalation through the nasal passage from a container of the powder held close up to the nose. Suitable formulations for nasal administration, wherein the carrier is a liquid, as for example, a nasal spray or nasal drops, include aqueous or oily solutions of the active ingredient.

Formulations suitable for vaginal administration may be presented as pessaries, tampons, creams, gels, pastes, foams or sprays containing in addition to the active ingredient such carriers as are known in the art to be appropriate.

Formulations suitable for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in freeze-dried (lyophilized) conditions requiring only the addition of the sterile liquid carrier, for example, water for injections, immediately prior to use. Extemporaneous injection solutions and suspensions may be prepared from sterile powders, granules, and tablets of the kind previously described.

Although buprenorphine is unstable when administered orally, the present invention contemplates the oral administration of buprenorphine in a suitable formulation that protects the compound from degradation in the stomach or lower alimentary canal thereby delivering a therapeutically effective amount of drug to the body.

I claim:

1. A method for treating chronic fatigue syndrome comprising administering to a patient in need thereof an effective amount of buprenorphine or a salt thereof.

2. The method of claim 1 comprising administering the buprenorphine or a salt thereof in a pharmaceutical composition.

3. The method of claim 2 wherein the composition is a sublingual lozenge.

4. The method of claim 2 wherein the composition is a transdermal gel.

5. The method of claim 4 wherein the transdermal gel is administered by application to a vascular area on the body.

6. The method of claim 1 wherein the effective amount of buprenorphine is between about 0.125 mg to about 3 mg per day.

7. The method of claim 1 wherein the buprenorphine or salt thereof is buprenorphine hydrochloride.

8. A method for treating fibromyalgia comprising administering to a patient in need thereof an effective amount of buprenorphine.

9. The method of claim 8 comprising administering the buprenorphine in a pharmaceutical composition.

10. The method of claim 9 wherein the composition is a sublingual lozenge.

11. The method of claim 9 wherein the composition is a transdermal gel.

12. The method of claim 11 wherein the transdermal gel is administered by application to a vascular area on the body.

13. The method of claim 8 wherein the effective amount of buprenorphine is between about 0.125 mg to about 3 mg per day.

14. The method of claim 8 wherein the buprenorphine or salt thereof is buprenorphine hydrochloride.

* * * * *